US010342797B2

(12) United States Patent
Mitchell et al.

(10) Patent No.: US 10,342,797 B2
(45) Date of Patent: Jul. 9, 2019

(54) SOLUBILITY OF THERAPEUTIC AGENTS

(71) Applicant: LivePet LLC, Austin, TX (US)

(72) Inventors: Ian Mitchell, Bartlesville, OK (US);
Daniel David Bensimon, Austin, TX (US); Ayyappan Subbiah, Bartlesville, OK (US); Rajashekharam Malyala, Camarillo, CA (US)

(73) Assignee: LivePet, LLC, Austin, TX (US)

( * ) Notice: Subject to any disclaimer, the term of this patent is extended or adjusted under 35 U.S.C. 154(b) by 0 days.

(21) Appl. No.: 15/341,146

(22) Filed: Nov. 2, 2016

(65) Prior Publication Data
US 2017/0258917 A1 Sep. 14, 2017

Related U.S. Application Data

(60) Provisional application No. 62/307,554, filed on Mar. 13, 2016.

(51) Int. Cl.
| | |
|---|---|
| *C07D 211/20* | (2006.01) |
| *A61K 31/517* | (2006.01) |
| *A61K 31/337* | (2006.01) |
| *A61K 31/4745* | (2006.01) |
| *A61K 31/138* | (2006.01) |
| *A61K 47/02* | (2006.01) |
| *A61K 47/14* | (2017.01) |
| *A61K 47/44* | (2017.01) |
| *A61K 31/365* | (2006.01) |
| *A61K 31/475* | (2006.01) |
| *A61K 31/565* | (2006.01) |

(52) U.S. Cl.
CPC .......... *A61K 31/517* (2013.01); *A61K 31/138* (2013.01); *A61K 31/337* (2013.01); *A61K 31/365* (2013.01); *A61K 31/475* (2013.01); *A61K 31/4745* (2013.01); *A61K 31/565* (2013.01); *A61K 47/02* (2013.01); *A61K 47/14* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 6,548,537 B1 | 4/2003 | Dai et al. | |
| 9,308,243 B2 | 4/2016 | Subbiah | |
| 2005/0036978 A1* | 2/2005 | Kozlowski | A61K 9/1611 424/78.17 |
| 2014/0140985 A1* | 5/2014 | Moussa | A23D 7/0053 424/125 |

FOREIGN PATENT DOCUMENTS

| | | |
|---|---|---|
| CN | 101250764 A | 8/2008 |
| CN | 102973636 A | 3/2013 |
| CN | 102552137 B | 4/2013 |
| CN | 102462723 B | 10/2013 |
| CN | 102793674 B | 11/2014 |
| WO | WO-2009023201 A1 | 2/2009 |
| WO | WO-2010062658 A1 | 6/2010 |
| WO | WO-2014145303 A1 | 9/2014 |

OTHER PUBLICATIONS

Cheng et al. (Naphthalene Adsorption and Desorption from Aqueous C60 Fullerene. Journal of Chemical and Engineering Data, vol. 49, No. 3, 2004).*
Prylutska et al. (C60 Fullerene as Synergistic Agent in Tumor-Inhibitory Doxorubicin Treatment. Drugs R D. Dec. 2014; 14(4): 333-340).*
Kupchan, S. M. et al., Triptolide and Tripdiolide, novel antileukemic diterpenoid triepoxides from Tripterygium wilfordii. Journal of American Chemical Society, 1972, 94, 7194-7195.
Kroto, H. W. et al., C60: Buckminsterfullerene. Nature, 1985, 318, 162-164.
Morris, R. E: Rapamycin: FK406's fraternal twin or distant cousin. Immunology today, 1991, 12, 138-140.
Kiviharju, T. M. et al., Antiproliferative and proapoptotic activities of Triptolide (PG490), a natural product entering alinical trials, on primary cultures of human prostatic epithelial cells. Clinical Cancer Research, 2002, 2666, 2666-2674.
Psaltopoulou, T. et al., Olive oil, the Mediterranean diet, and arterial blood pressure: the Greek European Prospective Investigation into Cancer and Nutrition (EPIC) study. American Journal of Clinical Nutrition, 2004, 80, 1012-1018.
Wu, S. et al., Clinical Observation on Effect of Triptolide Tablet inTreating Patients with Psoriasis Vulgaris. Chinese Journal of Integrative Medicine, 2005, 11, 147-148.
Gharbi, N. et al., [60]Fullerene is a Powerful Antioxidant in Vivo with No Acute or Subacute Toxicity. Nano Letters, 2005, 5, 2578-2585.
Peng, A. et al., Herbal Treatment for Renal Disease. Annals Academy of Medicine, Singapore 2005, 34, 44-51.
Phillips, P. A. et al., Triptolide Induces Pancreatic Cancer Cell Death via Inhibition of Heat Shock Protein 70. Cancer Research, 2007, 67, 9407-9416.
Partha, R. et al., Biomedical applications of functionalized fullerene-based nanomaterials. International Journal of Nanomedicine, 2009, 4, 261-275.
Liu, Z. et al., The Main Anticancer Bullets of the Chinese Medicinal Herb, Thunder God Vine. Molecules 2011, 16, 5283-5297.
Zhao, P. et al., Inclusion of celecoxib into fibrous ordered mesoporous carbon for enhanced oral bioavailability and reduced gastric irritancy. European Journal of Pharmaceutical Sciences, 2012, 45, 639-647.

(Continued)

Primary Examiner — Layla Soroush
(74) Attorney, Agent, or Firm — Meyertons, Hood, Kivlin, Kowert & Goetzel, P.C.

(57) ABSTRACT

Disclosed herein are methods and compositions to improve the solubility of therapeutic agents. In one embodiment, a method of improving solubility of a therapeutic agent includes mixing fullerene in a lipid solution to form a lipofullerene mixture, and mixing the therapeutic agent with the lipofullerene mixture.

16 Claims, 11 Drawing Sheets

(56) References Cited

OTHER PUBLICATIONS

Baati, T. et al., The prolongation of the lifespan of rats by repeated oral administration of [60]fullerene. Biomaterials, 2012, 33, 4936-4946.
Nakonechny, F. et al., Olive Oil-Based Delivery of Photosensitizers for Bacterial Eradication. Olive Oil—Constituents, Quality, Health Properties and Bioconversions. Dr. Dimitrios Boskou (Ed.), ISBN: 978-953-307-921-9. 2012, 471-492.
Chugh, R. et al., A Preclinical Evaluation of Minnelide as a Therapeutic Agent Against Pancreatic Cancer. Science Translational Medicine, 2012, 4, 156ps21.
Li, J. et al., Role of Nrf2 in protection against triptolide-induced toxicity in rat kidney cells. Toxicology Letters, 2012, 213, 194-202.
Zhou, Z-L. et al., Triptolide: structural modifications, structure-activity relationships, bioactivities, clinical development and mechanisms. Natural Product Reports, 2012, 29, 457-475.
Kalepu, S. et al., Oral lipid-baseddrugdeliverysystems—an overview. Acta Pharmaceutica Sinica B, 2013, 3, 361-372.
Singla, N. et al., Reproductive Toxicity of Triptolide in Male House Rat, *Rattus rattus*. The Scientific World Journal, 2014, Article ID 879405.
Wang, D. et al., Triptolide treatment reduces Alzheimer's disease (AD)-like pathology through inhibition of BACE1 in a transgenic mouse model of AD. Disease Models & Mechanisms, 2014, 7, 1385-1395.
Gong, X. et al., Absorption and Metabolism Characteristics of Triptolide as Determined by a Sensitive and Reliable LC-MS/MS Method. Molecules 2015, 20, 8928-8940.
Xu, H. et al., Antitumor effects of traditional Chinese medicine targeting the cellular apoptotic pathway. Drug Design, Development and Therapy. 2015, 9, 2735-2744.
Ioannis, P. et al., Tripterygium Wilfordii Extract (Triptolide) and Amygdalin Promotes Cell death in Cancer Cells: True or a Myth. American Journal of Cancer Prevention, 2015, 3, 77-83.
Liang, Z. et al., Triptolide improves systolic function and myocardial energy metabolism of diabetic cardiomyopathy in streptozotocin-induced diabetic rats. BMC Cardiovascular Disorders, 2015, 15, 42.
Allison AC, et al. A potent antioxidant and anti-inflammatory drug, as a possible treatment for Alzheimer's disease. Prog Neuropsychopharmacol Biol Psychiatry. Oct. 2001;25(7):1341-57.
Chen G, et al. Pharmacokinetic and pharmacodynamic study of triptolide-loaded liposome hydrogel patch under microneedles on rats with collagen-induced arthritis. Acta Pharm Sin B. Nov. 2015; 5(6): 569-576.
Chen H, et al. A study of microemulsion systems for transdermal delivery of triptolide. J Control Release. Aug. 27, 2004;98(3), abstract only.
Chen X, et al. A constituent of immunosuppressive Chinese herbal medicine, is a potent suppressor of dendritic-cell maturation and trafficking. Blood. Oct. 1, 2005; 106(7): 2409-2416.
Chen ZH, et al. Triptolide reduces proteinuria in experimental membranous nephropathy and protects against C5b-9-induced podocyte injury in vitro. Kidney Int. Jun. 2010;77(11):974-88.
Halaby R. Triptolide: Novel Anticancer Agent for Chemoresistant Cancer Cells that are Caspase-3 Deficient. J Mol Biol & Mol Imaging. 2015;2(1):1011.
Hoyle GW, et al. Identification of triptolide, a natural diterpenoid compound, as an inhibitor of lung inflammation. Am J Physiol Lung Cell Mol Physiol. Jun. 2010;298(6):L830-6.
Li XJ, et al. Triptolide: progress on research in pharmacodynamics and toxicology. J Ethnopharmacol. Aug. 8, 2014;155(1):67-79.
Liu J, et al. Metabolite profiling and identification of triptolide in rats. J Chromatogr B Analyt Technol Biomed Life Sci. Nov. 15, 2013;939:51-8.
Liu L, et al. Sex differences in subacute toxicity and hepatic microsomal metabolism of triptolide in rats. Toxicology. Apr. 30, 2010;271(1-2):57-63.
Liu M, et al. Anti-inflammatory effects of triptolide loaded poly(d,l-lactic acid) nanoparticles on adjuvant-induced arthritis in rats. J Ethnopharmacol. Feb. 28, 2005;97(2):219-25.
Liu Q. Triptolide and its expanding multiple pharmacological functions. Int Immunopharmacol. Mar. 2011;11(3):377-83.
Peng ZH, et al. Identification of in vivo and in vitro metabolites of triptolide by liquid chromatography-tandem mass spectrometry. J Pharm Biomed Anal. Nov. 2012;70:624-30.
Wang W, et al. Enhanced Antitumor Effect of Combined Triptolide and Ionizing Radiation. Clin Cancer Res. Aug. 15, 2007;13(16):4891-9.
Wang X, et al. Transdermal microemulsion drug delivery system for impairing male reproductive toxicity and enhancing efficacy of *Tripterygium wilfordii* Hook f. Fitoterapia. Jun. 2012;83(4):690-8. doi: 10.1016/j.fitote.2012.02.006. Epub Feb. 26, 2012.
Xu L, et al. Acute and subacute toxicity studies on triptolide and triptolide-loaded polymeric micelles following intravenous administration in rodents. Food Chem Toxicol. Jul. 2013;57:371-9.
Xu P, et al. Triptolide attenuated injury via inhibiting oxidative stress in Amyloid-Beta25-35-treated differentiated PC12 cells. Life Sciences. Oct. 2016; 145 (2016):19-26.
Zhang C, et al. Preparation and optimization of triptolide-loaded solid lipid nanoparticles for oral delivery with reduced gastric irritation. Molecules. Oct. 29, 2013;18(11):13340-56.
Zhang Y, et al. Research Progress on Intervention of Triptolide in Kidney Diseases. Curr Opin Complement Alternat Med. 2014; 1(1):e00004.
Zhou GX, et al. Apoptosis of human pancreatic cancer cells induced by Triptolide. World J Gastroenterol. Mar. 14, 2008; 14(10): 1504-1509.
Zhu LC. Triptolide. Chemistry 150, Fall 2008.
Zhu W, et al. A Small-Molecule Triptolide Suppresses Angiogenesis and Invasion of Human Anaplastic Thyroid Carcinoma Cells via Down-Regulation of the Nuclear Factor-B Pathway. Mol Pharmacol. Apr. 2009;75(4):812-9.

\* cited by examiner

SOLUBILITY OF THERAPEUTIC AGENTS

PRIORITY INFORMATION

This application claims priority to U.S. Provisional Application No. 62/307,554 filed on Mar. 13, 2016 entitled "Method of Making a Solution of Fullerene and Olive Oil Containing Triptolide and Its Therapeutic Applications" and is incorporated herein by reference.

BACKGROUND

Many important drugs have limited solubility in water, especially hydrophobic or lipophilic agents. In order to attain the full expected therapeutic effect of such agents, it is usually required that a solubilized form of the drug be administered to a patient. The poor water-solubility of these lipophilic agents often results in major difficulties in formulation, particularly when easily sterilizable and administrable homogeneous aqueous solutions are needed. Efficacious aqueous-based formulations are particularly problematic for systemic administration, in particular parenteral administration (i.e., injectable solutions) and for certain liquid preparations for, e.g., topical gynecologic, dermatologic ophthalmic, etc. use, and for use on the oral mucous membranes.

A number of methods for solubilizing drugs have been developed and most of them are based on the use of solvents or cosolvents, surfactants, complexing agents (for example, cyclodextrins or nicotinamide), or use of complicated drug carriers (for example, liposomes). Each of the above methods has one or more particular drawbacks. For example, the use of conventional surfactants and cyclodextrins to solubilize hydrophobic drugs has drawbacks related to surfactant and cyclodextrin toxicity and/or precipitation of the solubilized drugs once administered to the patient or when otherwise diluted in an aqueous environment. For therapeutic drugs that cannot be formulated as an aqueous solution, emulsions have oftentimes provided a cost-effective and therapeutically acceptable alternative. However, it is difficult to render emulsions sterile and/or endotoxin free for intravenous injection, and terminal sterilization by heat or filtration treatments is not suitable for all emulsions.

Disclosed herein methods to improve the solubility of therapeutic agents, preferably lipophilic agents, in mixtures comprising C60 fullerene and lipophilic solutions.

SUMMARY

Disclosed herein are methods and compositions to improve the solubility of therapeutic agents. In one embodiment, a method of improving solubility of a therapeutic agent includes mixing fullerene in a lipid solution to form a lipofullerene mixture, and mixing the therapeutic agent with the lipofullerene mixture. The therapeutic agents that may be used are anticancer agents, analgesics, anesthetics, antibiotics, antidepressants, antidiabetics, antifungals, antihypertensives, anti-inflammatories, immunosuppressives, sedatives, antianginal s, antipsychotics, antimanics, antiarthritics, antigouts, anticoagulants, antithrombolytics, anticonvulsants, antiparkinsons, antibacterials, antivirals, anti-infectives, and any combination thereof. The lipid solution that may be used are solutions of free fatty acids, esters of fatty acids, triacylglycerols, diacylglycerides, monoacylglycerides, lysophospholipids, caprylic triglycerides, vegetable oils, and combinations thereof. In some embodiments, fullerene and the lipid solution are mixed for about 12 hours to about 15 days in absence of light at a temperature of about 25° C. to about 45° C. In some embodiments, about 0.1 milligram to about 5 milligrams of fullerene is mixed with 1 mL of lipid solution. In other embodiments, about 0.01 milligram to about 10 milligrams of the therapeutic agent is mixed with 1 mL of the lipofullerene mixture.

In a further embodiment, a composition comprises a therapeutic agent, fullerene and a lipid solution, wherein the therapeutic agent is present from about 0.01 milligram to about 10 milligrams per 1 mL of the composition. The therapeutic agents that may be present in the composition are anticancer agents, analgesics, anesthetics, antibiotics, antidepressants, antidiabetics, antifungals, antihypertensives, anti-inflammatories, immunosuppressives, sedatives, antianginals, antipsychotics, antimanics, antiarthritics, antigouts, anticoagulants, antithrombolytics, anticonvulsants, antiparkinsons, antibacterials, antivirals, anti-infectives, and any combination thereof. The lipid solution that may be present in the composition are solutions of free fatty acids, esters of fatty acids, triacylglycerols, diacylglycerides, monoacylglycerides, lysophospholipids, caprylic triglycerides, vegetable oils, and combinations thereof.

In additional embodiment, a method of treating a subject in need thereof includes administering a pharmaceutical composition comprising a therapeutic agent, fullerene and a lipid solution, wherein the therapeutic agent is present from about 0.01 milligram to about 10 milligrams per 1 mL of the composition.

DETAILED DESCRIPTION

Figure 1:
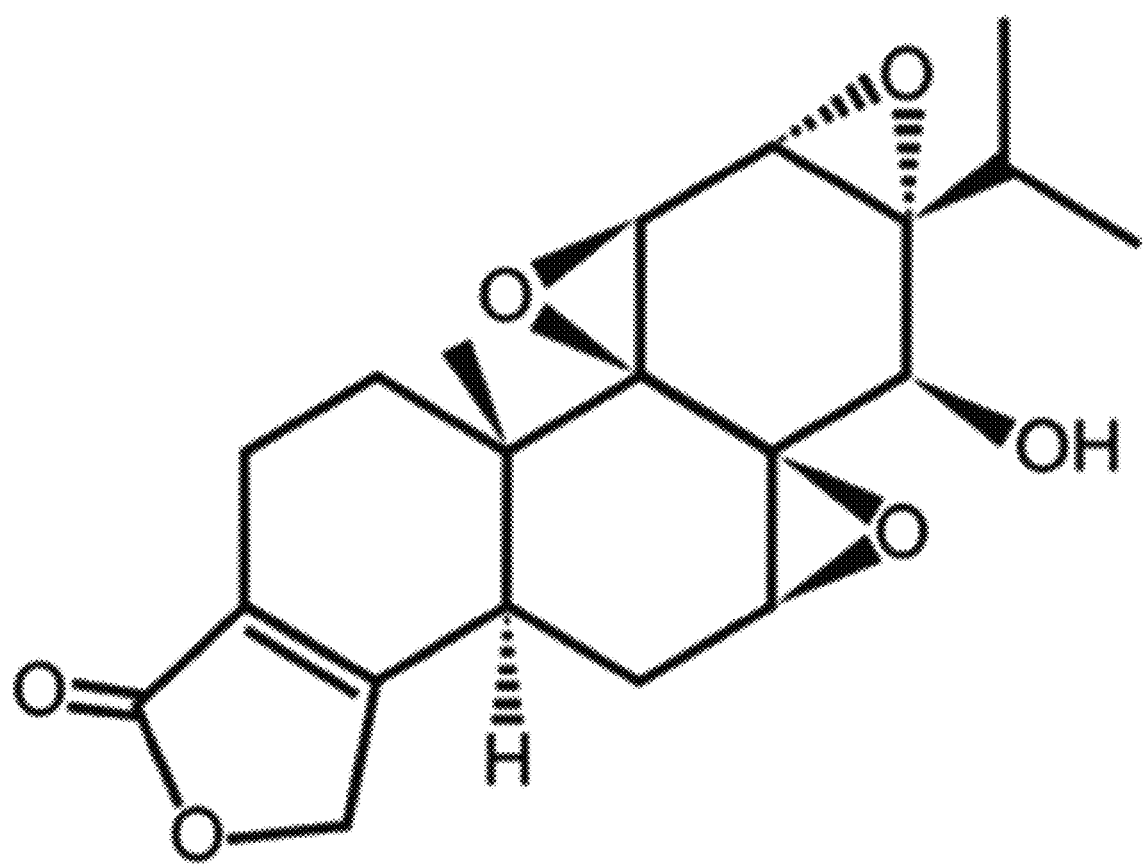
FIG. 1 shows a structure of triptolide.
Figure 2:
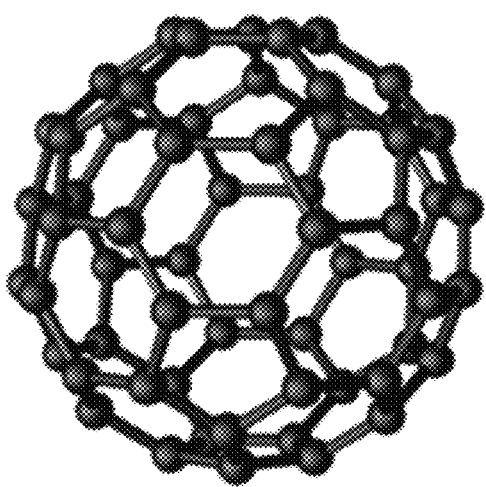
FIG. 2 shows a structure of fullerene C60, according to an embodiment.

Disclosed herein are methods to improve the solubility of lipophilic therapeutic agents. By virtue of a specific formulation, the therapeutic agents are stable and make it possible to reach a high degree of solubilization. Further, the compositions disclosed herein display increased bioavailability of the drug without impeding any chemical or functional properties of the drug.

The term "effective amount" as used herein generally refers to a sufficient amount of the pharmaceutically active agent that is added to decrease, prevent or inhibit the disease. The amount will vary for each compound and upon known factors related to the item or use to which the pharmaceutically active agent is applied.

The term "in need thereof" when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal is ill, will be ill, or is at risk of becoming ill, as the result of a condition that may be ameliorated or treated with the specified medical intervention.

In some embodiments, a method of improving solubility of a therapeutic agent includes mixing fullerene in a lipid solution to form a lipofullerene mixture, and mixing the therapeutic agent with the lipofullerene mixture.

As used herein, the term "lipid" includes phospholipids; free fatty acids, esters of fatty acids, triacylglycerols, diacylglycerides, monoacylglycerides, lysophospholipids, soaps, phosphatides, sterols and sterol esters, waxes, carotenoids, xanthophylls (e.g., oxycarotenoids), lycopene, vitamin E, coenzyme Q 10, lutein, BHA and BHT, hydrocarbons, and other lipids known to one of ordinary skill in the art.

In some embodiments, a lipid solution of fatty acids may be used. Fatty acids include saturated fatty acids, unsaturated fatty acids, polyunsaturated fatty acids. Non-limiting examples of unsaturated fatty acids include palmitoleic acid, margaric acid, stearic acid, oleic acid, octadecenoic acid, linoleic acid, gamma-linofeic acid, alpha linoleic acid, arachidic acid, eicosenoic acid, homogamma linoleic acid, arachidonic acid, eicosapenenoic acid, behenic, docosadsesioic acid, hesieicosapentaenoic, docosatetraenoic acid. Non-limiting examples of saturated fatty acids include lauric acid, palmitic acid, stearic acid, and myristic acid.

In some embodiments, a lipid solution of long chain fatty acids may be used. Fatty acids having 14 or more carbon atoms in the backbone are generally referred to as long chain fatty acids. Non-limiting examples include lauric acid, myristic acid, stearic acid, arachidic acid, behenic acid, oleic acid, linoleic acid, alpha-linolenic acid, arachidonic acid, eicosapentaenoic acid, docosahexaenoic acid, erucic acid, palmitic acid, adipic acid and any combinations thereof.

In some embodiments, a lipid solution of short and medium chain fatty acids may be used. The fatty acids having 14 or fewer carbon atoms in the backbone are generally referred to as short chain and medium chain fatty acids. Non-limiting examples include caproic acid, heptanoic acid, caprylic acid, nonanoic acid and capric acid.

In some embodiments, the lipid solution may be vegetable oils. Vegetable oils include olive oil, sunflower oil, corn oil, soybean oil, rapeseed oil, canola oil, safflower oil, peanut oil, avocado oil, cottonseed oil, argan oil, and gingerelli oil. In some embodiments, clarified butter (ghee) can also be used.

In some embodiments, the lipid solution may be caprylic triglycerides, such as miglyol 810, miglyol 812, miglyol 818; miglyol 829, and miglyol 840.

As used herein, "lipophilic therapeutic agent" in reference to a therapeutic agent or drug is intended to mean a sparingly (or poorly, slightly, scarcely) soluble biologically active or pharmaceutically active substance or antigen-comprising material, which has a therapeutic or prophylactic effect, and has utility in the treatment or prevention of diseases or disorders affecting mammals, including humans, or in the regulation of an animal or human physiological condition. The water-solubility of lipophilic drugs, at room temperature, is typically too low to make commercially proposable, sufficiently active or advantageous any aqueous preparations containing the compound as an active ingredient. Lipophilic therapeutic agents include substances, typically compounds, with little or no water solubility. Intrinsic water solubilities (i.e., water solubility of the unionized form) for lipophilic therapeutic agents usable in the present invention include, for example, those with a solubility of less than about 0.1% or 0.01% by weight, or, e.g., less than about 10 µg/mL.

Lipophilic therapeutic agents suitable for use in the formulations of the present invention are not particularly limited, as the method of the present invention is surprisingly capable of solubilizing a wide variety of lipophilic therapeutic agents. Therapeutic agents that can be utilized with the formulations of the present invention may be selected from a wide range of biologically and/or pharmacologically active substances, which lack adequate solubility in aqueous systems without a solubilizing agent. Such therapeutic agents include any agents having therapeutic or other value when administered to an animal, particularly to a mammal, such as drugs, prodrugs (i.e., agents than transform into active substances), nutrients (nutraceuticals), and cosmetics (cosmeceuticals). Such therapeutic agents can be utilized in formulations in accordance with the present invention so as to yield an effective therapeutic dose, e.g., for parenteral administration. The precise biological and/or pharmacological activity of the substance is immaterial, so long as the substance can be solubilized in the present formulations.

Specific non-limiting examples of lipophilic therapeutic agents that can be used in the formulations of the present invention include the following representative compounds, as well as their pharmaceutically acceptable salts, isomers, esters, ethers and other derivatives. These include anticancer agents, analgesics, anesthetics, antibiotics, antidepressants, antidiabetics, antifungals, antihypertensives, anti-inflammatories, immunosuppressives, sedatives, antianginal s, antipsychotics, antimanics, antiarthritics, antigouts, anticoagulants, antithrombolytics, anticonvulsants, antiparkinsons, antibacterials, antivirals, anti-infectives, and any combination thereof.

Non-limiting examples of the therapeutic agents include: analgesics and anti-inflammatory agents, such as aloxiprin, auranofin, azapropazone, benorylate, capsaicin, celecoxib, diclofenac, diflunisal, etodolac, fenbufen, fenoprofen calcium, flurbiprofen, ibuprofen, indomethacin, ketoprofen, ketorolac, leflunomide, meclofenaminc acid, mefenamic acid, nabumetone, naproxen, oxaprozin, oxyphenbutazone, phenylbutazone, piroxicam, rofecoxib, sulindac, tetrahydrocannabinol, tramadol and tromethamine;

anthelmintics, such as albendazole, bephenium hydroxynaphthoate, cambendazole, dichlorophen, ivermectin, mebendazole, oxamniquine, oxfendazole, oxantel embonate, praziquantel, pyrantel embonate and thiabendazole;

anti-arrhythmic agents, such as amiodarone HCl, disopyramide, flecainide acetate and quinidine sulfate;

anti-asthma agents, such as zileuton, zafirlukast, terbutaline sulfate, montelukast, and albuterol;

anti-bacterial agents, such as alatrofloxacin, azithromycin, baclofen, benzathine penicillin, cinoxacin, ciprofloxacin HCl, clarithromycin, clofazimine, cloxacillin, demeclocycline, dirithromycin, doxycycline, erythromycin, ethionamide, furazolidone, grepafloxacin, imipenem, levofloxacin, lorefloxacin, moxifloxacin HCl, nalidixic acid, nitrofurantoin, norfloxacin, ofloxacin, rifampicin, rifabutine, rifapentine, sparfloxacin, spiramycin, sulphabenzamide, sulphadoxine, sulphamerazine, sulphacetamide, sulphadiazine, sulphafurazole, sulphamethoxazole, sulphapyridine, tetracycline, trimethoprim, trovafloxacin, and vancomycin;

anti-viral agents, such as abacavir, amprenavir, delavirdine, efavirenz, indinavir, lamivudine, nelfinavir, nevirapine, ritonavir, saquinavir, and stavudine;

anti-coagulants, such as cilostazol, clopidogrel, dicumarol, dipyridamole, nicoumalone, oprelvekin, phenindione, ticlopidine, and tirofiban;

anti-depressants, such as amoxapine, bupropion, citalopram, clomipramine, fluoxetine HCl, maprotiline HCl, mianserin HCl, nortriptyline HCl, paroxetine HCl, sertraline HCl, trazodone HCl, trimipramine maleate, and venlafaxine HCl;

anti-diabetic agents, such as acetohexamide, chlorpropamide, glibenclamide, gliclazide, glipizide, glimepiride, miglitol, pioglitazone, repaglinide, rosiglitazone, tolazamide, tolbutamide and troglitazone;

anti-epileptic agents, such as beclamide, carbamazepine, clonazepam, thotoin, felbamate, fosphenytoin sodium, lamotrigine, methoin, methsuximide, methylphenobarbitone, oxcarbazepine, paramethadione, phenacemide, phenobarbitone, phenytoin, phensuximide, primidone, sulthiame, tiagabine HCl, topiramate, valproic acid, and vigabatrin;

anti-fungal agents, such as amphotericin, butenafine HCl, butoconazole nitrate, clotrimazole, econazole nitrate, fluconazole, flucytosine, griseofulvin, itraconazole, ketoconazole, miconazole, natamycin, nystatin, sulconazole nitrate, oxiconazole, terbinafine HCl, terconazole, tioconazole and undecenoic acid;

anti-gout agents, such as allopurinol, probenecid and sulphinpyrazone;

anti-hypertensive agents, such as amlodipine, benidipine, benezepril, candesartan, captopril, darodipine, dilitazem HCl, diazoxide, doxazosin HCl, enalapril, eposartan, losartan mesylate, felodipine, fenoldopam, fosenopril, guanabenz acetate, irbesartan, isradipine, lisinopril, minoxidil, nicardipine HCl, nifedipine, nimodipine, nisoldipine, phenoxybenzamine HCl, prazosin HCl, quinapril, reserpine, terazosin HCl, telmisartan, and valsartan;

anti-malarial agents, such as amodiaquine, chloroquine, chlorproguanil HCl, halofantrine HCl, mefloquine HCl, proguanil HCl, pyrimethamine and quinine sulfate;

anti-migraine agents, such as dihydroergotamine mesylate, ergotamine tartrate, frovatriptan, methysergide maleate, naratriptan HCl, pizotifen maleate, rizatriptan benzoate, sumatriptan succinate, and zolmitriptan;

anti-muscarinic agents, such as atropine, benzhexol HCl, biperiden, ethopropazine HCl, hyoscyamine, mepenzolate bromide, oxyphencyclimine HCl and tropicamide;

anti-neoplastic agents and immunosuppressants, such as aminoglutethimide, amsacrine, azathioprine, bicalutamide, bisantrene, busulfan, camptothecin, capecitabine, chlorambucil, cyclosporin, dacarbazine, ellipticine, estramustine, etoposide, irinotecan, lomustine, melphalan, mercaptopurine, methotrexate, mitomycin, mitotane, mitoxantrone, mofetil mycophenolate, nilutamide, paclitaxel, procarbazine HCl, sirolimus, tacrolimus, tamoxifen, teniposide, testolactone, topotecan HCl, docetaxel, fulvestrant, doxorubicin, vincristine, erlotinib, toremifene citrate, raloxifene, droloxifene, iodoxyfene, megestrol acetate, anasfrozole, letrazole, borazole, exemestane, flutamide, nilutamide, bicalutamide, cyproterone acetate, goserelin acetate, luprolide, finasteride, herceptin, methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, taxol, taxotere, teniposide, amsacrine, topotecan, epothilones, gefitinib, and erlotinib;

anti-protozoal agents, such as atovaquone, benznidazole, clioquinol, decoquinate, diiodohydroxyquinoline, diloxanide furoate, dinitolmide, furazolidone, metronidazole, nimorazole, nitrofurazone, ornidazole and tinidazole;

anti-thyroid agents, such as carbimazole and propylthiouracil;

anti-tussives, such as benzonatate;

anxiolytics, sedatives, hypnotics and neuroleptics, such as alprazolam, amylobarbitone, barbitone, bentazepam, bromazepam, bromperidol, brotizolam, butobarbitone, carbromal, chlordiazepoxide, chlormethiazole, chlorpromazine, chlorprothixene, clonazepam, clobazam, clotiazepam, clozapine, diazepam, droperidol, ethinamate, flunanisone, flunitrazepam, triflupromazine, flupenthixol decanoate, fluphenthixol decanoate, flurazepam, gabapentin, haloperidol, lorazepam, lormetazepam, medazepam, meprobamate, mesoridazine, methaqualone, methylphenidate, midazolam, molindone, nitrazepam, olanzapine, oxazepam, pentobarbitone, perphenazine pimozide, prochlorperazine, pseudoephedrine, quetiapine, risperidone, sertindole, sulpiride, temazepam, thioridazine, triazolam, zolpidem, and zopiclone;

β-blockers, such as acebutolol, alprenolol, atenolol, labetalol, metoprolol, nadolol, oxprenolol, pindolol and propranolol;

cardiac inotropic agents, such as anrinone, digitoxin, digoxin, enoximone, lanatoside C and medigoxin;

corticosteroids, such as beclomethasone, betamethasone, budesonide, cortisone acetate, desoxymethasone, dexamethasone, fludrocortisone acetate, flunisolide, fluocortolone, fluticasone propionate, hydrocortisone, methylprednisolone, prednisolone, prednisone and triamcinolone;

diuretics, such as acetazolamide, amiloride, bendroflumethiazide, bumetanide, chlorothiazide, chlorthalidone, ethacrynic acid, frusemide, metolazone, spironolactone and triamterene;

anti-parkinsonian agents, such as bromocriptine mesylate, lysuride maleate, pramipexole, ropinirole HCl, and tolcapone;

gastrointestinal agents, such as bisacodyl, cimetidine, cisapride, diphenoxylate HCl, domperidone, famotidine, lanosprazole, loperamide, mesalazine, nizatidine, omeprazole, ondansetron HCl, rabeprazole sodium, ranitidine HCl and sulphasalazine;

histamine H1 and H2-receptor antagonists, such as acrivastine, astemizole, chlorpheniramine, cinnarizine, cetrizine, clemastine fumarate, cyclizine, cyproheptadine HCl, dexchlorpheniramine, dimenhydrinate, fexofenadine, flunarizine HCl, loratadine, meclizine HCl, oxatomide, and terfenadine;

keratolytics, such as acetretin, calciprotriene, calcifediol, calcitriol, cholecalciferol, ergocalciferol, etretinate, retinoids, targretin, and tazarotene;

lipid regulating agents, such as atorvastatin, bezafibrate, cerivastatin, ciprofibrate, clofibrate, fenofibrate, fluvastatin, gemfibrozil, pravastatin, probucol, and simvastatin;

muscle relaxants, such as dantrolene sodium and tizanidine HCl;

nitrates and other anti-anginal agents, such as amyl nitrate, glyceryl trinitrate, isosorbide dinitrate, isosorbide mononitrate and pentaerythritol tetranitrate;

nutritional agents and fat-soluble vitamins, such as calcitriol, carotenes, dihydrotachysterol, essential fatty acids, non-essential fatty acids, phytonadiol, vitamin A, vitamin B2, vitamin D, vitamin E and vitamin K;

opioid analgesics, such as codeine, dextropropoxyphene, diamorphine, dihydrocodeine, fentanyl, meptazinol, methadone, morphine, nalbuphine and pentazocine;

sex hormones, such as clomiphene citrate, cortisone acetate, danazol, dehydroepiandrosterone, ethynyl estradiol, finasteride, fludrocortisone, fluoxymesterone, medroxyprogesterone acetate, megestrol acetate, mestranol, methyltestosterone, norethisterone, norgestrel, oestradiol, conjugated estrogens, progesterone, rimexolone, stanozolol, stilbestrol, testosterone and tibolone;

stimulants, such as amphetamine, dexamphetamine, dexfenfluramine, fenfluramine and mazindol;

other therapeutic agents include erectile dysfunction improvement agents, anti-osteoporosis agents, anti-obesity agents, cognition enhancers, anti-urinary incontinence agents, anti-benign prostate hypertrophy agents, such as becaplermin, donepezil HCl, L-thryroxine, methoxsalen, verteporfin, physostigmine, pyridostigmine, raloxifene HCl, sibutramine HCl, sildenafil citrate, tacrine, tamsulosin HCl, and tolterodine.

The term "fullerene" is used generally herein to refer to any closed cage carbon compound containing both six- and five-member carbon rings independent of size and is intended to include the abundant lower molecular weight C60 and C70 fullerenes, larger known fullerenes including C76, C78, C84 and higher molecular weight fullerenes C2N where N is 50 or more (giant fullerenes) and which may optionally be nested and/or multi-concentric fullerenes. The term is intended to include "solvent extractable fullerenes" as that term is understood in the art (generally including the lower molecular weight fullerenes that are soluble in toluene or xylene) and to include higher molecular weight fullerenes that cannot be extracted, including giant fullerenes which can be at least as large as C400. Additional classes of fullerenes include, among others specifically noted herein, endohedral fullerenes contains one or more elements, particularly one or more metal elements, and heterofullerenes in which one or more carbons of the fullerene cage are substituted with a non-carbon element, such as B or N. The term fullerenic material is used generally to refer to a material that contains a mixture of fullerenes or a mixture of one or more fullerenes with non-fullerenes, e.g., amorphous carbonaceous materials that may for example be formed during fullerene synthesis by any known method and includes raw or crude preparations of fullerenes, such as combustion soot as well as raw or crude preparations of fullerenes that have been at least partially purified, for example, by extraction and/or sublimation.

In some embodiments, carbon nanomaterials may also be used in place of fullerenes. Examples of carbon nanomaterials include, but are not limited to, fullerenes, single-walled carbon nanotubes (SWNTs), multiple-walled carbon nanotubes (MWNTs), nanotubules, and nested carbon structures with dimensions on the order of nanometers In some embodiments, the method to improve the solubility of a therapeutic agent involves mixing fullerene in a lipid solution to form a lipofullerene mixture. Mixing can be done by sonication, vortexing, shaking, or using a blender to mix, or any combination thereof. The fullerene that may be used is a C60 fullerene. The amount of fullerene that may be mixed is from about 0.1 milligram to about 5 milligrams, about 0.1 milligram to about 4 milligrams, about 0.1 milligram to about 3 milligrams, about 0.1 milligram to about 2 milligrams, about 0.1 milligram to about 1 milligram per 1 mL of lipid solution.

In some embodiments, the mixing the fullerene and the lipid solution may be carried out for a period of about 6 hours to about 15 days, about 6 hours to about 10 days, about 12 hours to about 15 days, about 12 hours to about 10 days, about 12 hours to about 7 days, about 12 hours to about 3 days. The mixing is usually performed in darkness, without exposure to light. In some embodiments, the temperature during the mixing period may be maintained at about 25° C. to about 45° C., about 25° C. to about 40° C., about 25° C. to about 38° C., or about 25° C. to about 30° C.

In some embodiments, the lipofullerene mixture is filtered to remove any undissolved fullerene, before adding the therapeutic agent.

In some embodiments, the method further includes mixing a therapeutic agent disclosed herein with the lipofullerene mixture. The amount of the therapeutic agent that may be mixed is about 0.01 milligram to about 10 milligrams, about 0.01 milligram to about 5 milligrams, about 0.01 milligram to about 3 milligrams, about 0.01 milligram to about 2 milligrams, or about 0.01 milligram to about 1 milligram of the therapeutic agent per 1 mL of the lipofullerene mixture.

Mixing the therapeutic agent in the lipofullerene mixture can be done by sonication, vortexing, shaking, or using a blender to mix, or any combination thereof. Mixing may be performed under inert conditions and in darkness, without exposure to light. The inert conditions may be established by mixing under nitrogen or argon atmosphere.

In some embodiments, the therapeutic agent and the lipofullerene mixture may be vortexed or shaken for about 30 minutes to about 7 days, about 30 minutes to about 96 hours, for about 30 minutes to about 48 hours, for about 1 hour to about 24 hours, or for about 1 hour to about 12 hours. In some embodiments, the therapeutic agent and the lipofullerene mixture may be optionally sonicated before vortexing. The sonication may be performed for about 30 seconds to about 1 hour, about 30 seconds to about 1 hour, about 30 seconds to about 30 minutes, about 30 seconds to about 15 minutes, or about 30 seconds to about 5 minutes.

Disclosed herein are compositions of lipophilic therapeutic agents that have been solubilized in fullerene/lipid solution mixtures. In some embodiments, a composition comprises a therapeutic agent, fullerene and a lipid solution, wherein the therapeutic agent is present from about 0.01 milligram to about 10 milligrams per 1 mL of the composition. The therapeutic agent may be any therapeutic agent disclosed herein, such as anticancer agents, analgesics, anesthetics, antibiotics, antidepressants, antidiabetics, antifungals, antihypertensives, anti-inflammatories, immunosuppressives, sedatives, antianginal s, antipsychotics, antimanics, antiarthritics, antigouts, anticoagulants, antithrombolytics, anticonvulsants, antiparkinsons, antibacterials, antivirals, anti-infectives, and any combination thereof. Further, the lipid solution may be any lipid solution disclosed herein, such as solutions of free fatty acids, esters of fatty acids, triacylglycerols, diacylglycerides, monoacylglycerides, lysophospholipids, caprylic triglycerides, vegetable oils, and combinations thereof.

In some embodiments, the therapeutic agent is present from about 0.01 milligram to about 10 milligrams, about 0.01 milligram to about 5 milligrams, about 0.01 milligram to about 3 milligrams, about 0.01 milligram to about 2 milligrams, or about 0.01 milligram to about 1 milligram per 1 mL of the composition. In other embodiments, the fullerene is present from about 0.1 milligram to about 5 milligrams, about 0.1 milligram to about 4 milligrams, about 0.1 milligram to about 3 milligrams, about 0.1 milligram to about 2 milligrams, about 0.1 milligram to about 1 milligram per 1 mL of the composition.

The composition may also contain optional, additional ingredients to improve the dispersivity and dissolution of the substituted alkanoic acid. Suitable additional components include surfactants such as, for example, polyglyceryl esters of fatty acids, polyglycolyzed glycerides, propylene glycol esters, mono- and di-glycerides, sorbitan fatty acid esters, polyoxyethylene sorbitan fatty acid esters, polyoxyethylene sorbitol esters, polyoxyethylene adds, polyoxyethylene alcohols, and mixtures thereof. A preferred class of surfactants for use in combination with the lipophilic solvents is the polyoxyethylene sorbitan fatty acid esters.

Formulations containing the lipophilic therapeutic agents of the present invention can be solid dosage forms which include, but are not limited to, softgels, tablets, capsules, cachets, pellets, pills, powders and granules; topical dosage forms which include, but are not limited to, solutions, powders, fluid emulsions, fluid suspensions, semisolids, ointments, pastes, creams, gels and jellies, and foams; and parenteral dosage forms which include, but are not limited to, solutions, suspensions, emulsions, and dry powder. In some embodiments, a single dose may comprise one or more softgels, tablets, capsules, cachets, pellets, pills, or the like. Specific examples include, for example, a dose comprising 1, 2, 3, or 4 softgels, tablets, capsules, cachets, pellets, pills or the like.

In some embodiments, the composition may be a pharmaceutical composition comprising a therapeutic agent, fullerene and a lipid solution, wherein the therapeutic agent is present from about 0.01 milligram to about 10 milligrams per 1 mL of the composition. The therapeutic agent and the lipid solution may be any of therapeutic agents/lipid solutions disclosed herein.

In some embodiments, the pharmaceutical compositions may be formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. The pharmaceutical compositions may include excipients, such as without limitation, binders, coating, disintegrants, fillers, diluents, flavors, colors, lubricants, glidants, preservatives, sorbents, sweeteners, conjugated linoleic acid (CLA), gelatin, beeswax, purified water, glycerol, any type of oil, including, without limitation, fish oil or soybean oil, or the like. Pharmaceutical compositions can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols. It will further be appreciated by an ordinary practitioner of the art that the term also encompasses those pharmaceutical compositions that contain an admixture of two or more pharmacologically active compounds, such compounds being administered, for example, as a combination therapy.

A pharmaceutical composition may be provided as sustained-release or timed-release formulations. Such formulations may release a bolus of a compound from the formulation at a desired time, or may ensure a relatively constant amount of the compound present in the dosage is released over a given period of time. Terms such as "sustained release," "controlled release," or "timed release" and the like are widely used in the pharmaceutical arts and are readily understood by a practitioner of ordinary skill in the art.

Chemical compositions described herein are typically administered orally but any suitable route of administration may be employed for providing a subject with an effective dosage of drugs of the chemical compositions described herein. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In certain embodiments, it may be advantageous that the compositions described herein be administered orally.

The compositions may include those compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the drugs used in the present invention are conveniently delivered in the form of an aerosol spray presentation from pressurized packs or nebulizers. The compounds may also be delivered as powders which may be formulated and the powder composition may be inhaled with the aid of an insufflation powder inhaler device.

Suitable topical formulations for use in the present embodiments may include transdermal devices, aerosols, creams, ointments, lotions, dusting powders, gels, and the like.

In practical use, drugs used can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

The pharmaceutical preparations may be manufactured in a manner which is itself known to one skilled in the art, for example, by means of conventional mixing, granulating, dragee-making, softgel encapsulation, dissolving, extracting, or lyophilizing processes. Thus, pharmaceutical preparations for oral use may be obtained by combining the active compounds with solid and semi-solid excipients and suitable preservatives. Optionally, the resulting mixture may be ground and processed. The resulting mixture of granules may be used, after adding suitable auxiliaries, if desired or necessary, to obtain tablets, softgels, lozenges, capsules, or dragee cores.

The compounds are typically administered in admixture with suitable pharmaceutical diluents, excipients, or carriers (collectively referred to herein as "pharmacologically inert carriers") suitably selected with respect to the intended form of administration, that is, oral tablets, capsules, elixirs, syrups and the like, and consistent with conventional pharmaceutical practices.

Suitable excipients may be fillers such as saccharides (e.g., lactose, sucrose, or mannose), sugar alcohols (e.g., mannitol or sorbitol), cellulose preparations and/or calcium phosphates (e.g., tricalcium phosphate or calcium hydrogen phosphate). In addition binders may be used such as starch paste (e.g., maize or corn starch, wheat starch, rice starch, potato starch, gelatin, tragacanth, methyl cellulose, hydroxypropylmethylcellulose, sodium carboxymethylcellulose, and/or polyvinyl pyrrolidone). Disintegrating agents may be added (e.g., the above-mentioned starches) as well as carboxymethyl-starch, cross-linked polyvinyl pyrrolidone, agar, or alginic acid or a salt thereof (e.g., sodium alginate). Auxiliaries are, above all, flow-regulating agents and lubricants (e.g., silica, talc, stearic acid or salts thereof, such as magnesium stearate or calcium stearate, and/or polyethylene glycol, or PEG). Dragee cores are provided with suitable coatings, which, if desired, are resistant to gastric juices. Softgelatin capsules ("softgels") are provided with suitable coatings, which, typically, contain gelatin and/or suitable edible dye(s). Animal component-free and kosher gelatin capsules may be particularly suitable for the embodiments described herein for wide availability of usage and consumption. For this purpose, concentrated saccharide solutions may be used, which may optionally contain gum arabic, talc, polyvinyl pyrrolidone, polyethylene glycol (PEG) and/or titanium dioxide, lacquer solutions and suitable organic solvents or solvent mixtures, including dimethylsulfoxide (DMSO), tetrahydrofuran (THF), acetone, ethanol, or other suitable solvents and co-solvents. In order to produce coatings resistant to gastric juices, solutions of suitable cellulose preparations such as acetylcellulose phthalate or hydroxypropylmethyl-cellulose phthalate, may be used. Dye stuffs or pigments may be added to the tablets or dragee coatings or softgelatin capsules, for example, for identification or in order to characterize combinations of active compound doses, or to disguise the capsule contents for usage in clinical or other studies.

Other pharmaceutical preparations that may be used orally include push-fit capsules made of gelatin, as well as soft, thermally sealed capsules made of gelatin and a plasticizer such as glycerol or sorbitol. The push-fit capsules may contain the active compounds in the form of granules that may be mixed with fillers such as, for example, lactose, binders such as starches, and/or lubricants such as talc or magnesium stearate and, optionally, stabilizers and/or preservatives. In soft capsules, the active compounds may be dissolved or suspended in suitable liquids, such as fatty oils such as rice bran oil or peanut oil or palm oil, or liquid paraffin. In some embodiments, stabilizers and preservatives may be added.

Liquid dosage forms for oral administration can contain coloring and flavoring to increase subject acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable formulations for parenteral administration include, but are not limited to, suspensions of the active compounds as appropriate oily injection suspensions may be administered, particularly suitable for intramuscular injection. Suitable lipophilic solvents, co-solvents (such as DMSO or ethanol), and/or vehicles including fatty oils, for example, rice bran oil or peanut oil and/or palm oil, or synthetic fatty acid esters, for example, ethyl oleate or triglycerides, may be used. Liposomal formulations, in which mixtures of the chemical compositions described herein with, for example, egg yolk phosphotidylcholine (E-PC), may be made for injection. Optionally, the suspension may contain stabilizers, for example, antioxidants such as BHT, and/or preservatives, such as benzyl alcohol.

Also disclosed herein are lipofullerene compositions that can be used as a base solution to solubilize any therapeutic agent. In some embodiments, a composition comprises fullerene and a lipid solution, wherein the fullerene is present from about 0.1 milligram to about 5 milligrams per 1 mL of the composition.

In some embodiments, the lipofullerene base solution may itself have therapeutic properties. Lipofullerene C60 have been shown to have high anti-oxidant activity in vivo, protecting rats from $CCl_4$ exposure, thus suggesting anti-oxidant capabilities of lipofullerene C60. The ability to scavenge free radicals by lipofullerene C60 by attaching to the double bonds is also known. It has been suggested that the mode of action is the attenuation of or decrease of age-associated oxidative stress. When the lipofullerene base is used in combination with the therapeutic agent, the resulting compositions may demonstrate synergistic effects. Further, the lipofullerene base are stable and homogenous solutions of fullerenes in olive oil can be stored for 3 years (probably even more) without degradation.

Also disclosed herein are methods of treating with a subject with the compositions described herein. In some embodiments, a method of treating a subject in need thereof includes administering a pharmaceutical composition comprising an effective amount of a therapeutic agent, fullerene and a lipid solution, wherein the therapeutic agent is present from about 0.01 milligram to about 10 milligrams per 1 mL of the composition. The therapeutic agent may be any therapeutic agent disclosed herein, such as anticancer agents, analgesics, anesthetics, antibiotics, antidepressants, antidiabetics, antifungals, antihypertensives, anti-inflammatories, immunosuppressives, sedatives, antianginals, antipsychotics, antimanics, antiarthritics, antigouts, anticoagulants, antithrombolytics, anticonvulsants, antiparkinsons, antibacterials, antivirals, anti-infectives, and any combination thereof. The lipid solution may be any lipid, such as fatty acids, esters of fatty acids, triacylglycerols, diacylglycerides, monoacylglycerides, lysophospholipids, caprylic triglycerides, vegetable oils, and combinations thereof.

In some embodiments, the therapeutic agents described herein may be administered at a dosage level up to conventional dosage levels, but will typically be less than about 50 mL per day. Suitable dosage levels for therapeutic agents described herein may be about 0.01 mg to 10 mg per kg body weight of the patient per day, from about 0.1 mg to 1 mg per kg body weight of the patient per day, or from about 0.01 mg to 0.1 mg per kg body weight of the patient per day. The therapeutic agents may be administered on a regimen of up to 6 times per day, between about 1 to 4 times per day, or once per day.

In some embodiments, the therapeutic agents disclosed herein are used to treat cancer. The cancer can be a hematological tumor such as, e.g., acute myeloid leukemia, chronic myeloid leukemia, Hodgkin lymphoma, non-Hodgkin lymphoma, multiple myeloma, acute lymphoblastic leukemia, or chronic lymphocytic leukemia. In some embodiments, the cancer can be a solid tumor selected from the group consisting of breast cancer, melanoma, lung cancer, ovarian cancer, pancreatic cancer, colorectal cancer, prostate cancer, brain cancer, gastroesophageal cancer, and kidney cancer.

In some embodiments, the therapeutic agents disclosed herein are used to treat neurodegenerative diseases. The neurodegenerative diseases may be Alzheimer's disease, senile dementia, dementia with Lewy Bodies, Parkinson's disease, Huntington's disease, amyotrophic lateral sclerosis, and combination thereof. In some embodiments, the neurodegenerative diseases may be Mediterranean fever, Muckle-Wells syndrome, idiopathic myeloma, amyloid polyneuropathy, amyloid cardiomyopathy, systemic neuritic amyloidosis, amyloid polyneuropathy, hereditary cerebral hemorrhage with amyloidosis, Down's syndrome, Scrapie, Creutzfeldt-Jacob disease, Kuru, Gerstamnn-Straussler-Scheinker syndrome, medullary carcinoma of the thyroid, isolated atrial amyloid, p2-microglobulin amyloid in dialysis patients, inclusion body myositis, p2-amyloid deposits in muscle wasting disease, type II diabetes, and combinations thereof.

In yet another specific embodiment, therapeutic agents is administered at a dose of approximately 280 micrograms/day, wherein the patient is administered a single dose per day. The maximum injection volume in a single dose is approximately one-third of the estimated target tumor volume. The single dose is administered every other day for approximately three weeks. After this cycle, a subsequent cycle may begin approximately one week later. The treatment regime may include three cycles, each cycle being spaced apart by approximately one week. In some embodiments, the effective dose of the therapeutic agent is between about 100 and 2000 micrograms in 50 mL/week, for example approximately 100, 200, 335, 500, 700, 930, 1240 micrograms in 50 mL/week. After this cycle, a subsequent cycle may begin approximately 1, 2, 4, 6, or 12 weeks after the previous dose. The treatment regime may include 1, 2, 3, 4, 5, or 6 cycles, each cycle being spaced apart by approximately 1, 2, 4, 6, or 12 months.

The pharmaceutical compositions of the present invention can be administered in the conventional manner by any route where they are active. Administration can be systemic, parenteral, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration of the composition of the present invention (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

In some embodiments, the pharmaceutical compositions of the current invention is administered in combination with radiation therapy, surgery and/or chemotherapy. For example, the pharmaceutical compositions may be administered in combination with radiation therapy and cisplatin (Platinol), fluo-rouracil (5-FU, Adrucil), carboplatin (Paraplatin), and/or paclitaxel (Taxol). Treatment with the pharmaceutical composition of the current invention may allow use of lower doses of radiation and/or less frequent radiation treatments, which may for example, reduce the incidence of severe sore throat that impedes swallowing function potentially resulting in undesired weight loss or dehydration.

In some embodiments, the pharmaceutical compositions of the current invention can be administered before surgery, concurrent with surgery, or after surgery.

It is to be understood that even though numerous characteristics and advantages of various embodiments of the present disclosure have been set forth in the foregoing materials, together with details of the structure and function of various embodiments of the invention, this detailed description is illustrative only, and changes may be made in detail, especially in matters of structure and arrangements of parts within the principles of the embodiments of the present invention to the full extent indicated by the broad general meaning of the terms disclosed.

EXAMPLES

Example 1: Preparation of Lipofullerene Base

About 1000 mL of extra virgin olive oil was stirred with 0.8 grams of pure fullerene C60 in a 2 liter conical flask. The stirring process was carried out at about 38° C. The stirring process was carried out for about 14 days in the absence of light. After the completion of stirring, the solution was filtered using quantitative 103 slow filter paper to remove undissolved fullerene C60, if any. The filtrate obtained was called lipofullerene base.

Example 2: Preparation of Lipofullerene Base

About 1000 mL of MIGLYOL 810N was stirred with 0.8 grams of pure fullerene C60 in a 2 liter conical flask. The stirring process was carried out at about 38° C. The stirring process was carried out for about 14 days in the absence of light. After the completion of stirring, the solution was filtered using quantitative 103 slow filter paper to remove undissolved fullerene C60, if any. The process was repeated with other caprylic tryglycerides, such as MIGLYOL 812N, MIGLYOL 8129, and MIGLYOL 840.

Example 3: Preparation of Lipofullerene Base

About 2.4 gms of C60 fullerene was added to 1000 mL of olive oil and mixed in a blender at full speed for 2 minutes. Later, the mixture was stirred for additional 3 days in the dark. After the completion of stirring, the solution was filtered using quantitative 103 slow filter paper to remove undissolved fullerene C60, if any.

Example 4: Solubilizing Triptolide

About 2 gm of triptolide was dissolved in about 1000 mL of lipofullerene base of Example 1 in a nitrogen gas atmosphere and stirred for 2 hours. The solubility of the drug was confirmed by a turbidometer.

The procedure was repeated using 1000 mL of olive oil alone and the solubility of triptolide was 0.5 gm/1000 mL.

Example 5: Protective Effect of Triptolide (Solubilized in C60-Olive Oil) on Amyloid Beta Peptide (Aβ) Induced Neurodegeneration in 3D Organotypic Brain Slice Cultures Timed pregnant female mice (Harlan BALB/C strain) were acclimatized for a week to reduce the stress of transportation. Following the initial rest period, animals were weighed and the animals were verified of their health status. 5-7 d following birth of the pups, the pups were cold anesthetized (use of anesthetics interfere with the viability of slices; cold anesthesia is acceptable published method) before organs were excised and placed in either ice-cold organ preservation solution (liver, lung, kidney, and brain) or in oxygenized ice-cold Krebs-Henseleit buffer supplemented with 10 mM Hepes, 25 mM D-glucose, and 25 mM. Organs obtained from the pups were chilled for 10 min at 2° C. before slicing. Brain tissue slices from Hippocampal-Entorhinal Cortex (HEC) region were generated with a McIllwain Tissue Chopper and the slices were placed onto Millicell inserts (3-4 slices in each insert) in 6 well plate containing 1.7 mL of Dulbecco's modified Eagle's medium, and allowed to pre-incubate for 1 h in $O_2$:$CO_2$, 95:5, at 37° C. The slices thereafter were allowed to mature in the dish containing tissue culture medium for a defined time period.

Figure 3:
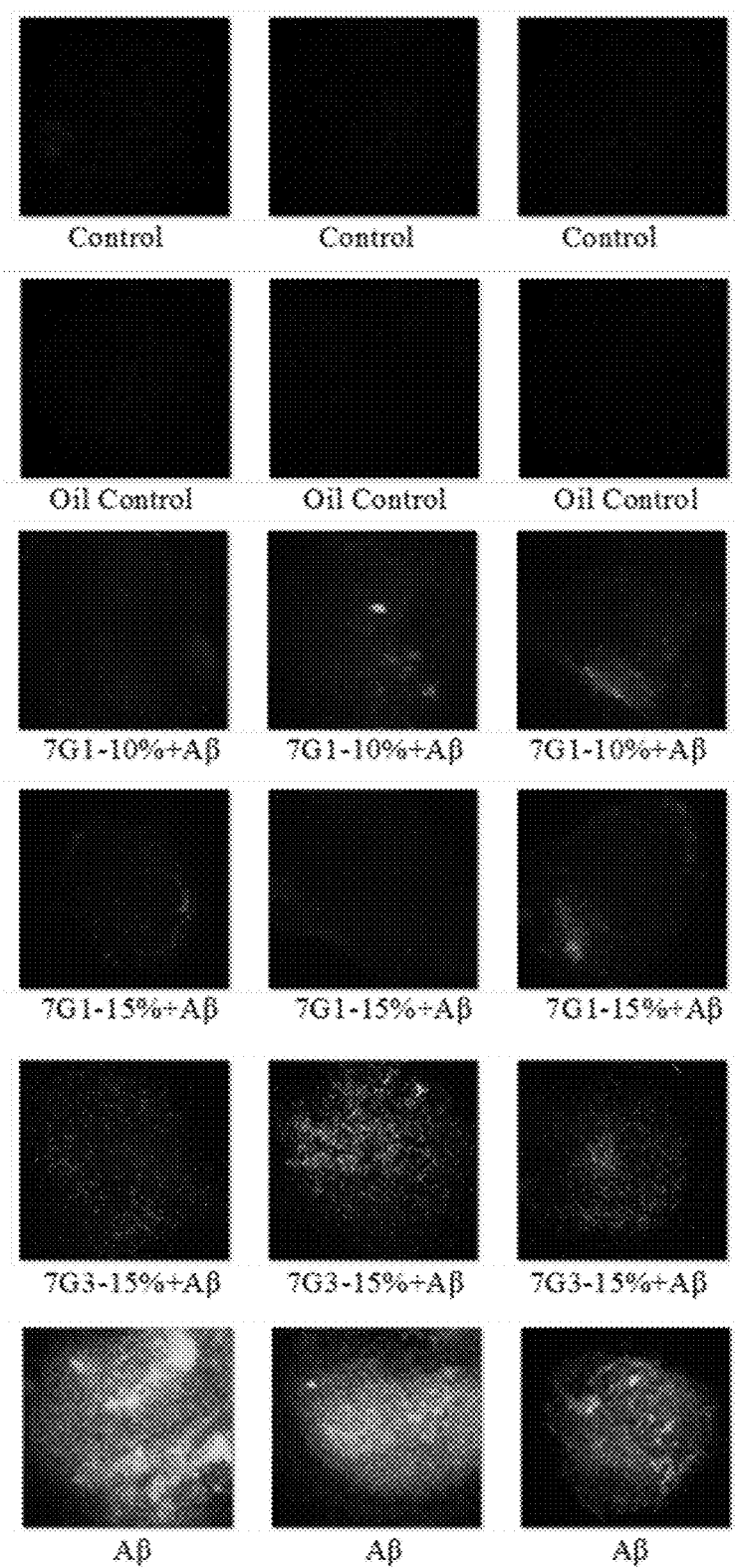
FIG. 3 shows co-treatment of HEC brain tissue slices with triptolide and Amyloid β peptide (Aβ) at various doses. Fluorescence of Sytox green dye was measured after 48 hr treatment. Triptolide was solubilized in C60-olive oil; 7G-1=0.1 mg of triptolide/mL of C60-oliveoil base; and 7G-3=0.5 mg of triptolide/mL of C60-oliveoil base.
Figure 4:
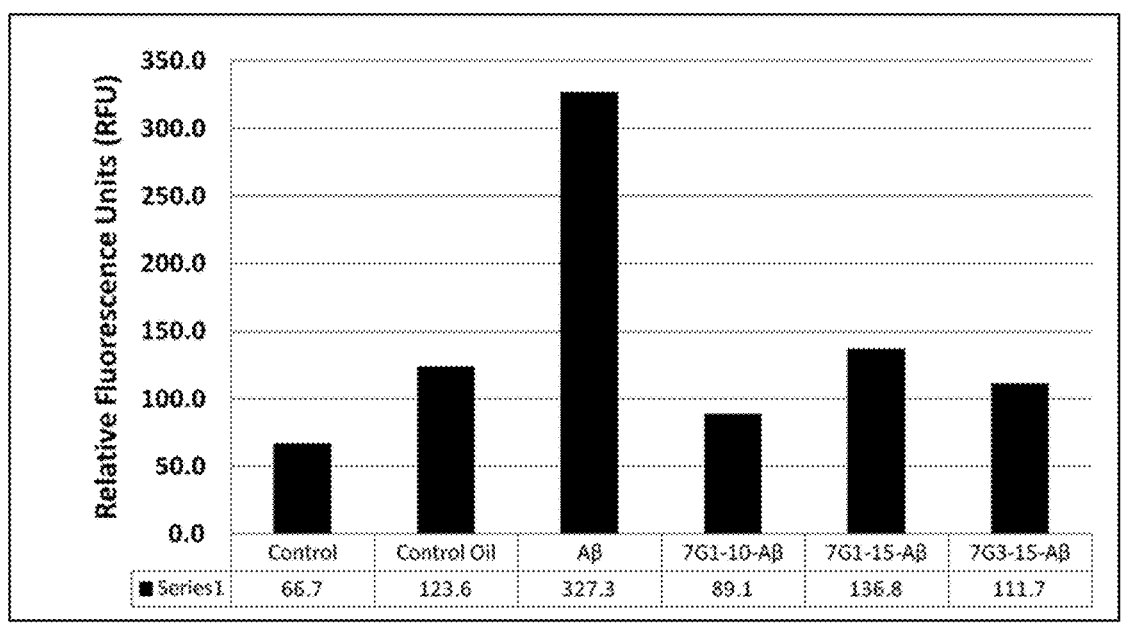
FIG. 4 shows Relative Fluorescence Units after 48 hr co-treatment with triptolide (solubilized in C60-olive oil) and Aβ at various doses.
Figure 5:
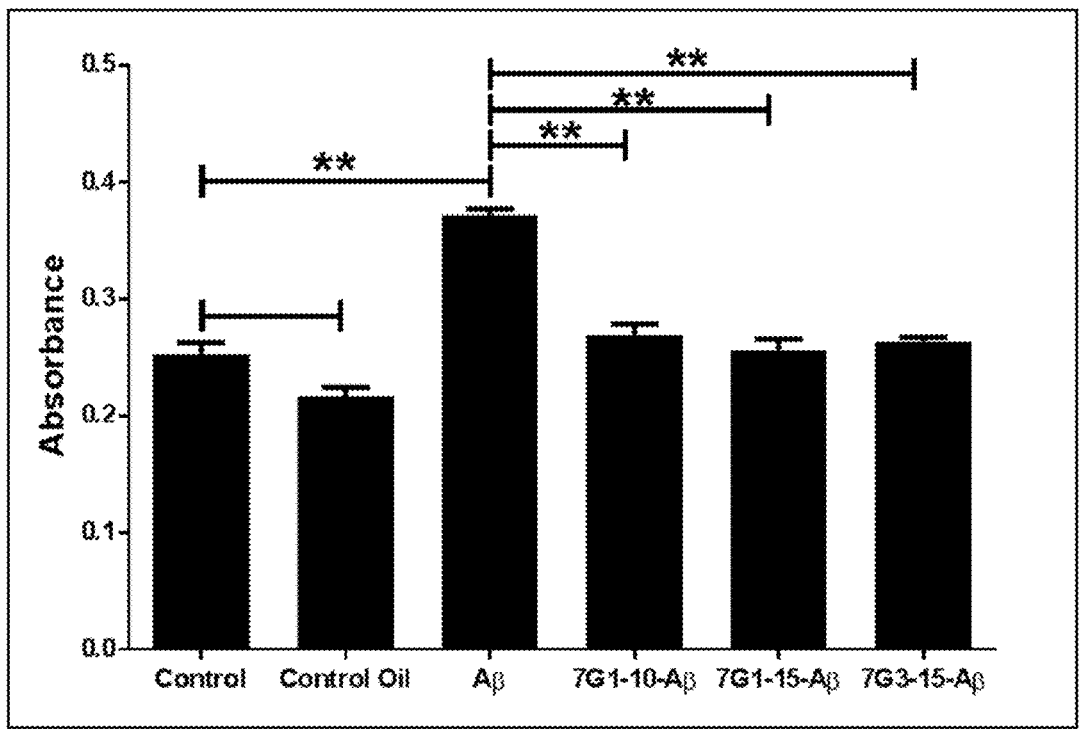
FIG. 5 shows lactate dehydrogenase (LDH) values in the culture media (A) and in the tissue slices (B) after co-treatment with triptolide (solubilized in C60-olive oil) and Aβ at various doses for 48 hr.
Figure 5:
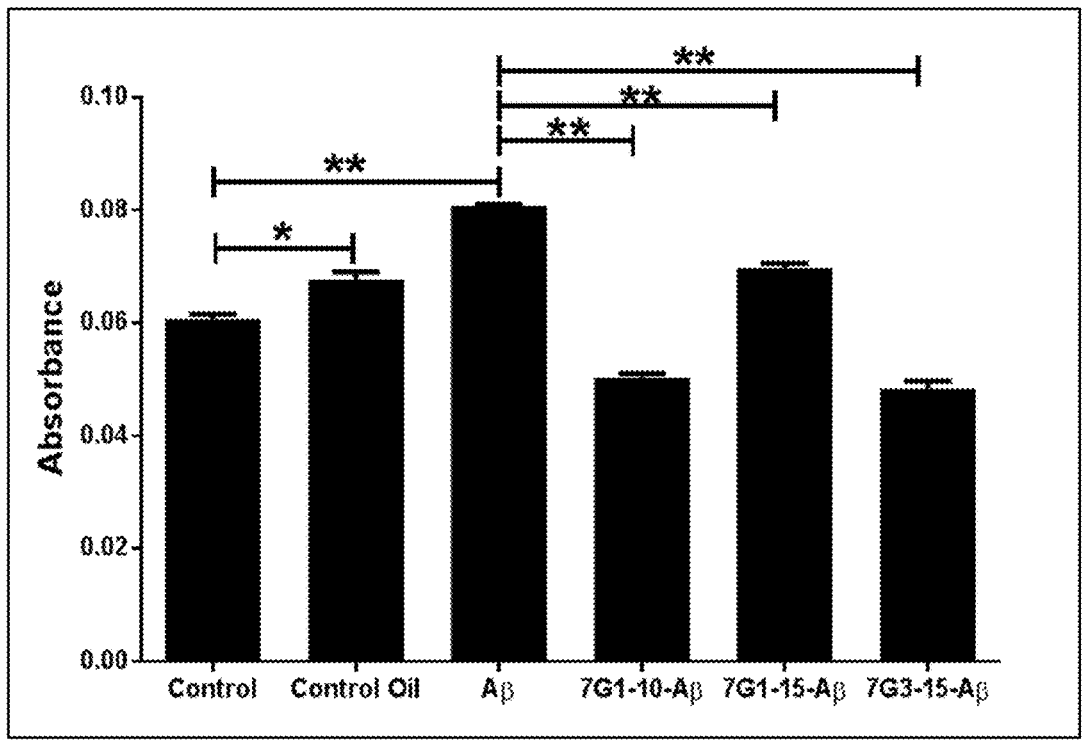

After 14-16 days of culture and maturation, plates with HEC brain slice inserts were treated with Aβ (5 μm) and 7G1 (0.1 mg of triptolide/1 mL of C60-Olive oil base) or 7G3 (0.5 mg of triptolide/1 mL of C60-Olive oil base) for 48 hrs. The volume of 7G1 and 7G3 added to the media were about 10% of the total media volume (designated as 7G1-10) or to about 15% of the total media volume (designated as 7G1-15 or 7G3-15), as indicated in FIGS. 3-5. Degenerating neurons were detected in brain slices with Sytox green dye (binds to dead cells), added at initial stage. Sytox green dye uptake in each slice was assessed by capturing fluorescence in a fluoresecent plate reader (BioTek). Media aliquots were analyzed for Lactate dehydrogenase (LDH) enzyme level, an indicator of cell membrane damage and death. Tissue protein was determined in centrifuged extracts of slice homogenates with a Bicinchoninic acid (BCA)-based method as required.

Results shown in FIG. 3 and FIG. 4 demonstrated that when solubilized triptolide was co-treated with amyloid β peptide, the neurons were protected from degeneration, as measured by Sytox green dye fluorescence. The viability of neurons was also measured by detecting the LDH levels (FIG. 5).

Figure 6:
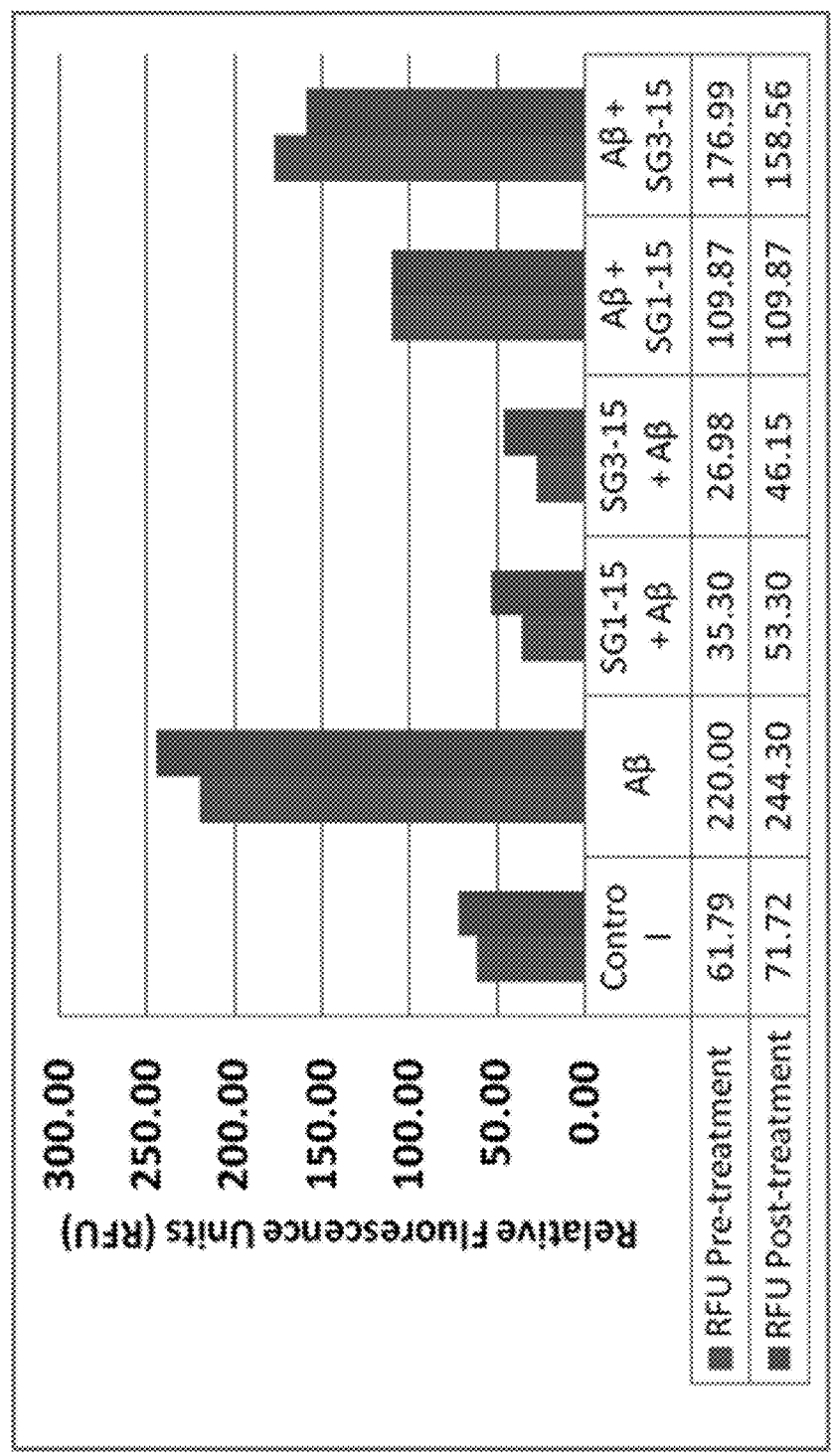
FIG. 6 shows the effect of pre- and post-treatment of triptolide (solubilized in C60-olive oil) on HEC brain slice cultures exposed to Amyloid beta peptide (Aβ) (5 μM) for 96 hrs, as measured by Relative Fluorescence Units (RFU).

To further analyze the protective effect of solubilized triptolide, brain tissue slices were pre-treated with SG1/SG3 or post-treated after amyloid β peptide exposure. FIG. 6 shows effect of SG1-15 (stock solution of 0.1 mg of triptolide/1 mL of C60-Olive oil base added to the media to about 15% of the total media volume) and SG3-15 (stock solution of 0.5 mg of triptolide/1 mL of C60-Olive oil base added to the media to about 15% of the total media volume) in HEC brain slice cultures exposed to Amyloid beta peptide (Aβ) (5 μM) for 96 hrs. A representative graph of Sytox green dye labeling in brain slices is shown as Relative Fluorescence Units (RFU). Vehicle-treated slices reveal normal background fluorescence and minimal cellular labeling on pre-treatment (48 hr) and post-treatment (48 hr). Pre- and post-treatment by SG1 and SG3 demonstrate evident suppression of brain injury compared to Aβ alone. Based on RFU values it could be concluded pre-treatment with SG1 and SG3 is protective than post-treatment.

Figure 7:
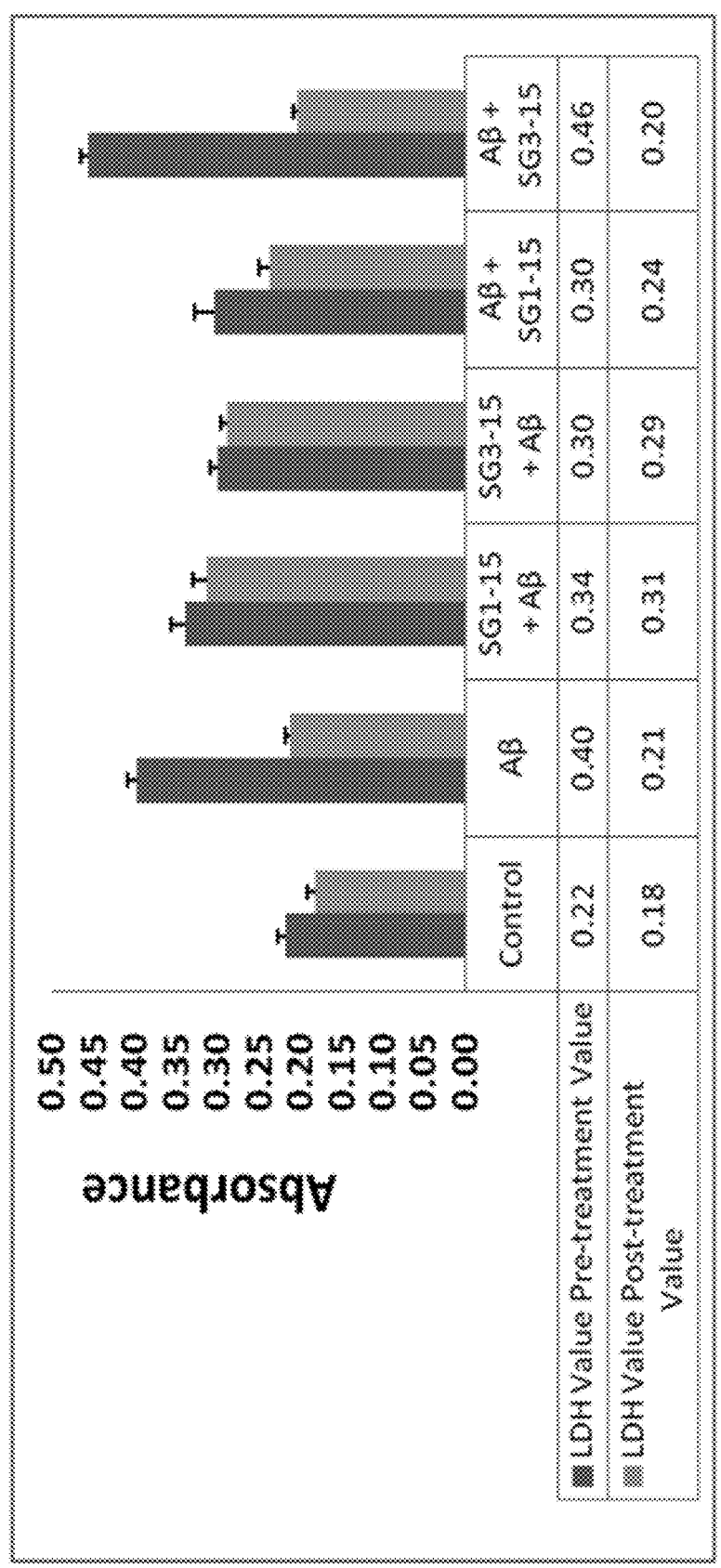
FIG. 7 shows the effect of pre- and post-treatment of triptolide (solubilized in C60-olive oil) on HEC brain slice cultures exposed to Amyloid beta peptide (Aβ) (5 μM) for 96 hrs, as measured by LDH levels.

The protective effect was also confirmed by measuring the LDH levels in the media of the brain tissue cultures (FIG. 7). Increase in media lactate dehydrogenase (LDH) level was observed in HEC brain slice cultures exposed to Aβ alone. Pretreatment with SG1 and SG3 was able to abrogate the effects of Aβ. Results shown in FIG. 6 and FIG. 7 demonstrate that pre-treatment confers better protection and reduces brain injury.

Example 6: Cytotoxicity Studies

Figure 8:
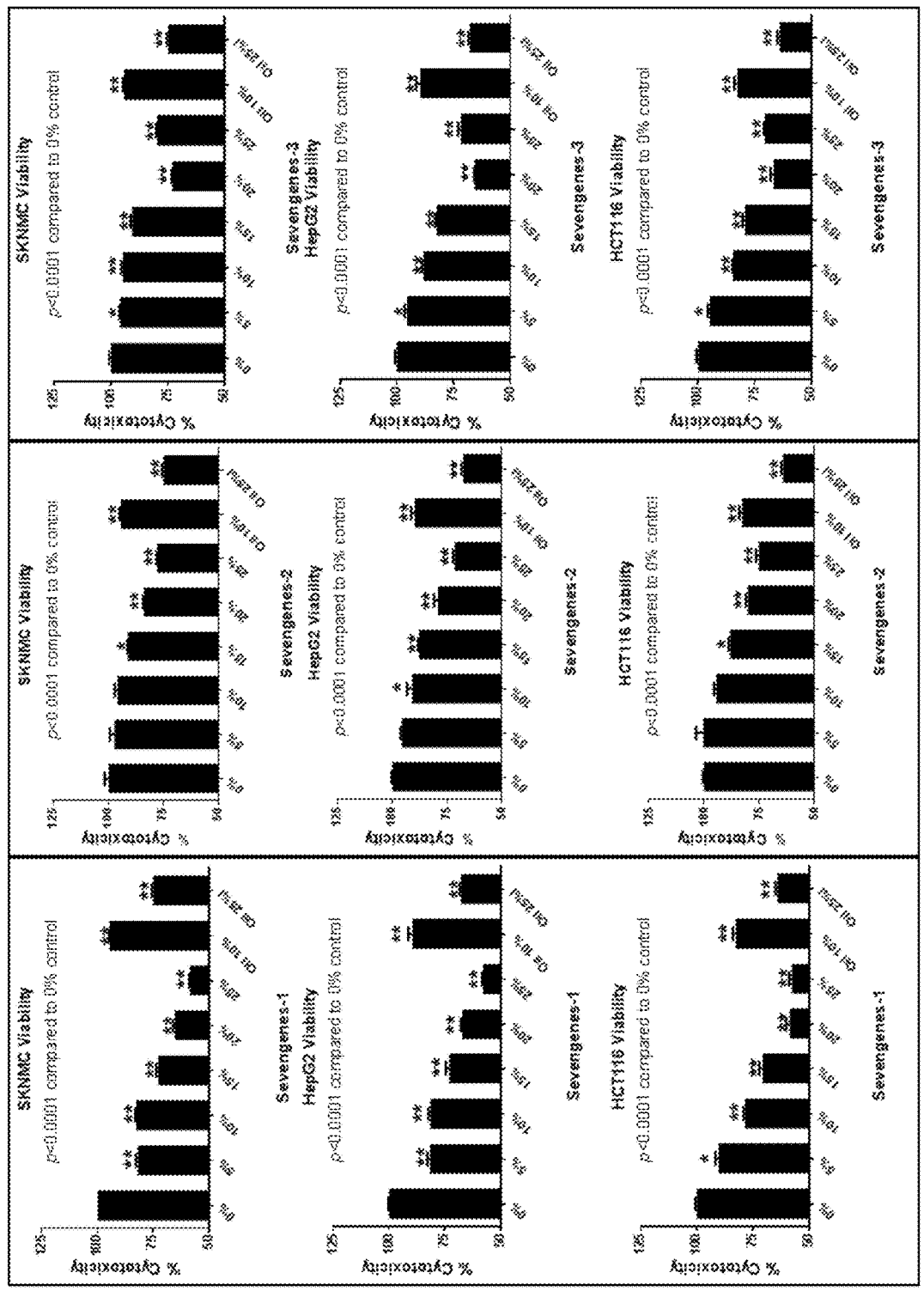
FIG. 8 shows percent change in viability of cells treated with triptolide (solubilized in C60-olive oil) for 24 hr at different concentrations, as assessed by Viability Assays (GF-AFC) (n=3).
Figure 9:
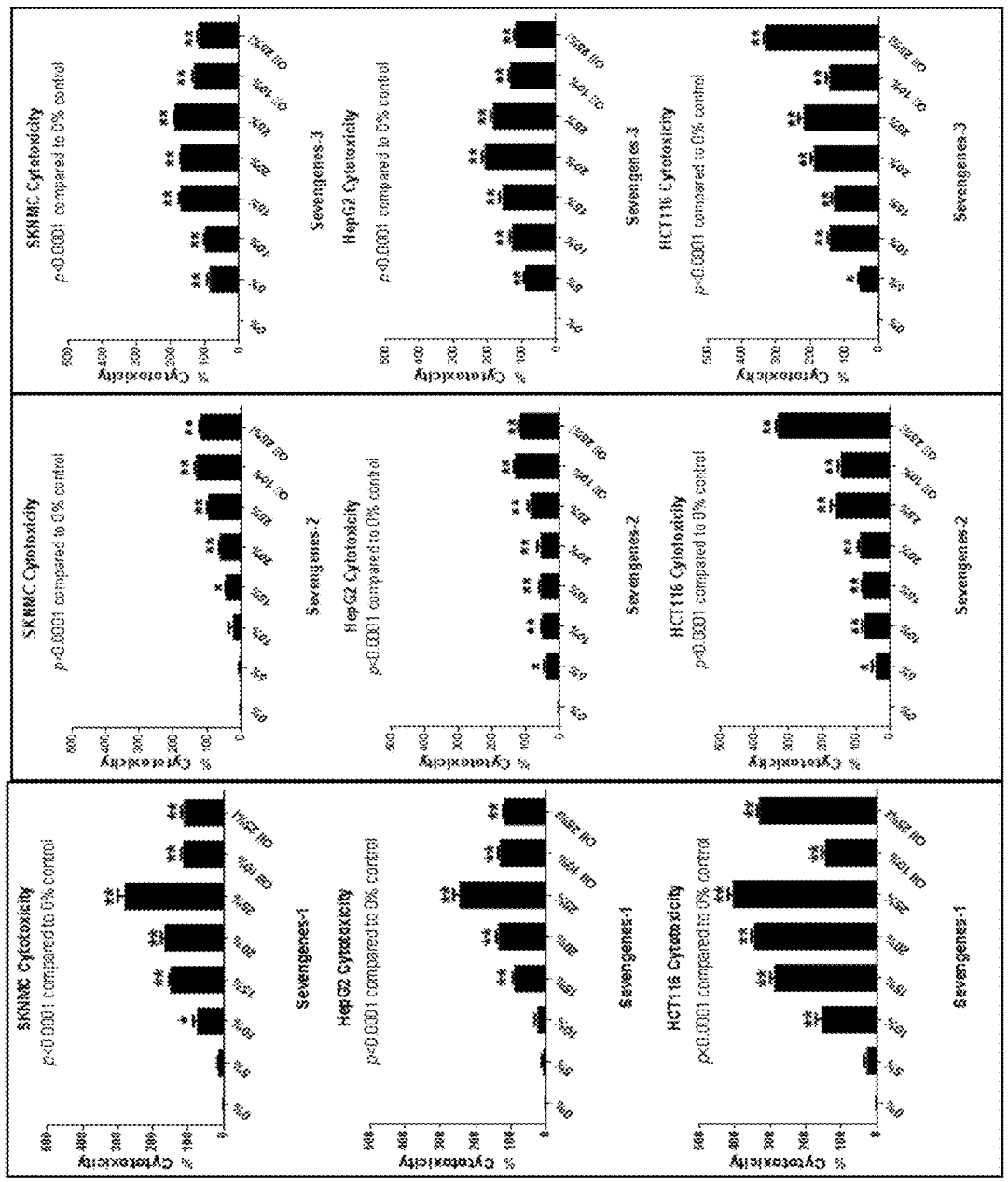
FIG. 9 shows percent change in number of cells treated with triptolide (solubilized in C60-olive oil) for 24 hr at different concentrations, as assessed by Cytotoxicity Assays (CellTox™ Green Dye) (n=3).

SKNMC, HepG2, and HCT116 cells were seeded on a 96 well plate and cultured for 24 hrs under standard culture conditions. The cells were exposed to the Sevengenes-1 (0.1 mg of triptolide/1 mL of C60-Olive oil base), Sevengenes-2 (0.25 mg of triptolide/1 mL of C60-Olive oil base), and Sevengenes-3 (0.1 mg of triptolide/1 mL of C60-Olive oil base) for 24 hrs. The volume/amount of Sevengenes-1, 2, 3 added to media were about 0%, 5%, 10%, 15%, 20%, and 25% of the total volume of the media. Cell cytotoxicity and viability were analyzed by using GF-AFC Substrate and CellTox™ Green Dye (Promega) which is a fluorescent-based assay which measures cell cytotoxicity and viability. All reactions were run in triplicate and results plotted with SEM as the % activity relative to the no compound control. Controls included no cells, cells with no test substance, and cells with the compound vehicle solvent. At the end of the treatment duration of 24 hrs, 20 μl of Viability/Cytotoxicity Reagent containing both GF-AFC Substrate and CellTox™ Green Dye substrate was added to all wells. The reaction mixture was briefly mixed by orbital shaking (300-500 rpm for ~30 seconds) and then incubated for 30 minutes at 37° C. Fluorescence was measured at the following two wavelength sets: 400Ex/505Em (Viability) and 485Ex/520Em (Cytotoxicity). The percentage of viable cells, and dead cells expression were calculated (FIG. 8 and FIG. 9) as the relative ratio of absorbance to the control to provide percentage of cell cytolysis.

Viability and cytotoxicity results showed that, in all three cell lines (SKNMC, HepG2, and HCT116) cell viability was reduced and cytotoxicity increased after 24 hours of exposure to Sevengenes-1, 2, and 3. Sevengenes-1, 2, and 3 at all doses were effective when compared to the control group, with a p value<0.0001. (** asterisk indicates doses that are significantly effective than the control).

Example 7: Cytotoxicity Studies

Figure 10:
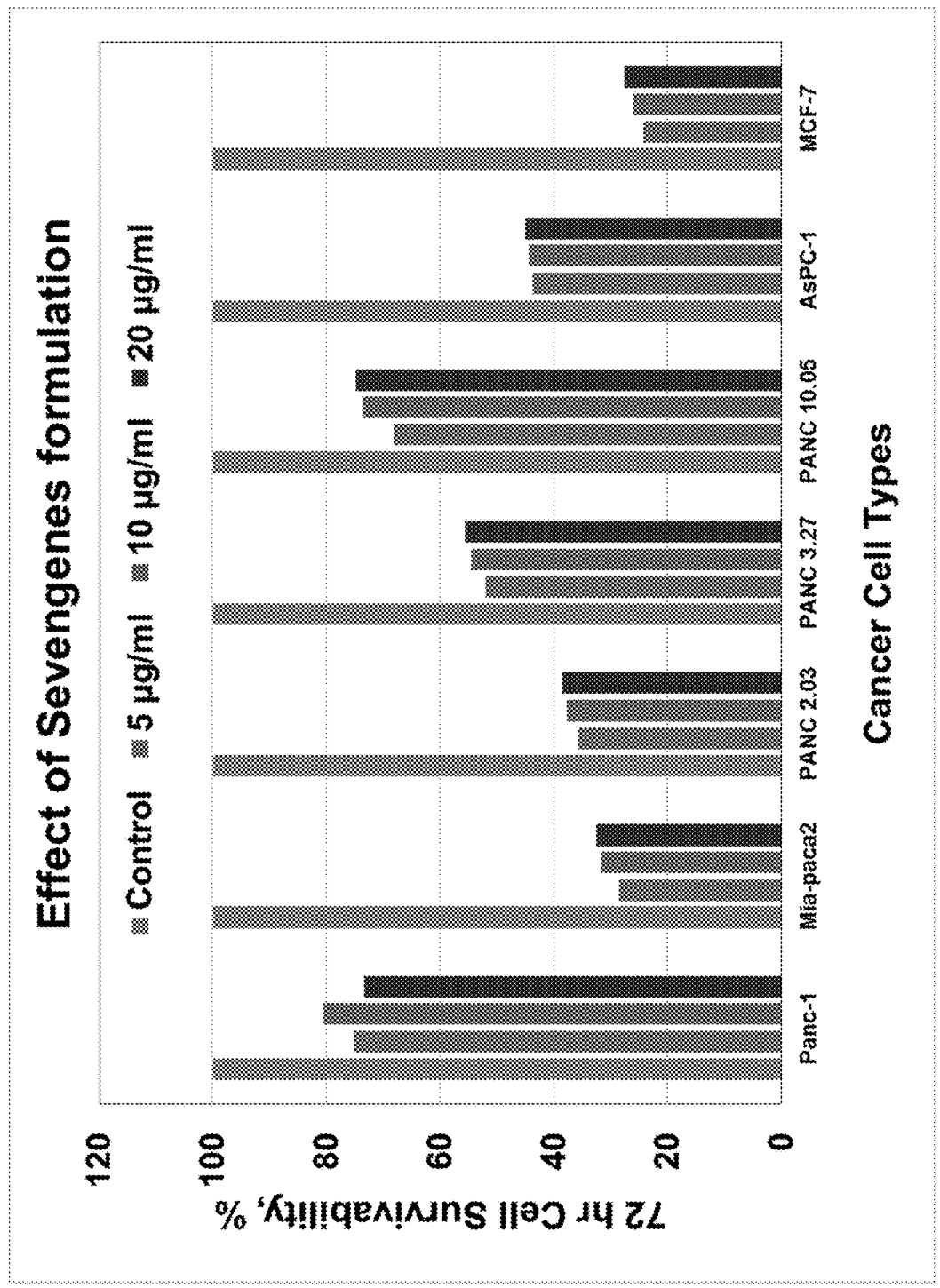
FIG. 10 shows cell proliferation studies after exposure to triptolide (solubilized in C60-olive oil), as measured by MTT assays.

MTT assay was used to analyze the effect of triptolide (1 mg of triptolide/1 mL of C60-olive oil base) on induced cytotoxicity. Cells were seeded at a density of 1000 cells/100 µL in a 96-well plate, grown for 24 h. The cells were then exposed to different concentrations of triptolide as indicated in FIG. 10. After 24/48 h of incubation at 37° C., 3-(4,5-methylthiazol-2-yl)-2,5-diphenyltetrazolium bromide (MTT) (11 µL/well of a 5 mg/mL solution in PBS) in 100 µL of media without serum was added for 4 h. Solubilization of the converted purple formazan dye was accomplished by adding 100 µL/well of acid-isopropanol and shaking for 20 min at 37° C. The reaction product was quantified by measuring the absorbance at 540-590 nm using Synergy 4 Multi-Detection Microplate Reader (Biotek Instruments, Inc., Highland Park, Vt.). All samples were assayed at least in triplicate. Cell growth was expressed as percent of control, and group-wise comparisons were made using ANOVA with Tukey's post-hoc correction. A p value of ≤0.05 was considered statistically significant. Results showed (FIG. 10) that triptolide solubilized in C60-olive oil significantly inhibited the proliferation of various cancer cells in vitro, demonstrating the efficacy of the drug after solubilization.

Example 8: Xenograft Studies

Figure 11:
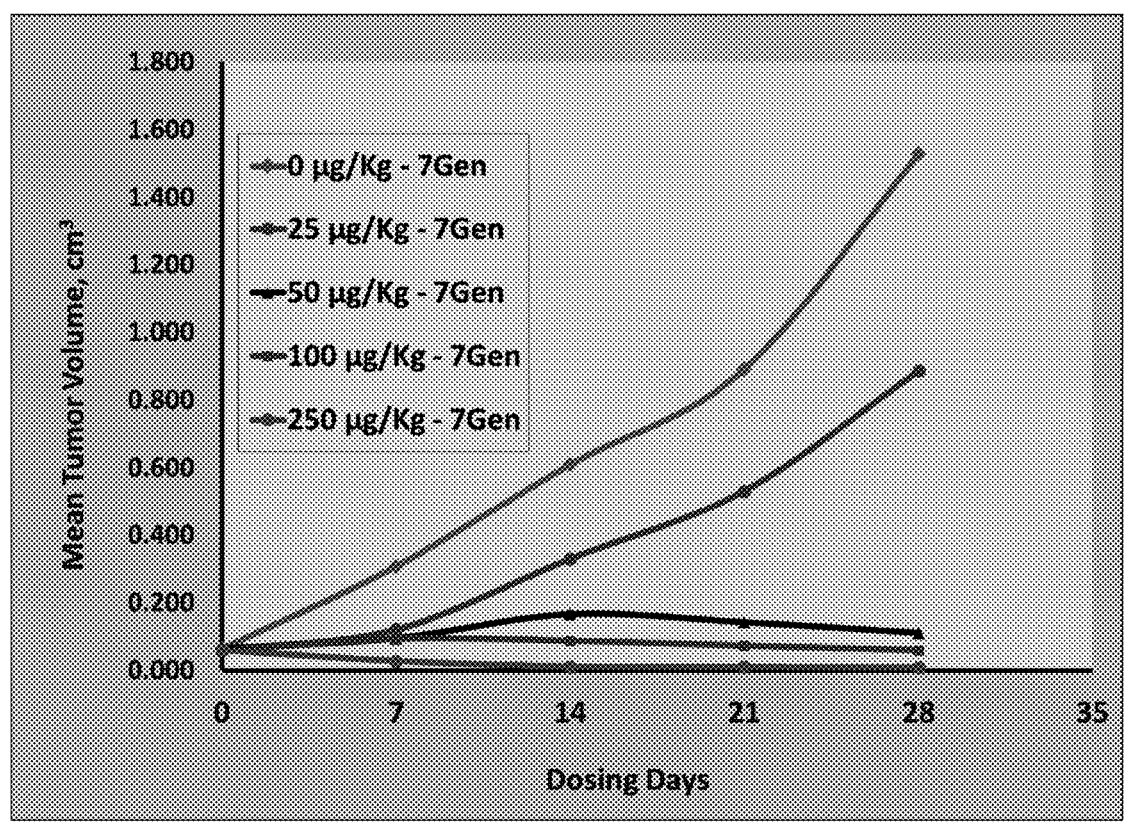
FIG. 11 depicts the effect of triptolide (solubilized in C60-olive oil) in xenograft studies in nude mice (n=5).

AsPC-1 cells were purchased from American Type Culture Collection (ATCC). Cells were harvested from sub-confluent cultures after brief exposure to 0.25% trypsin and 0.2% EDTA. The cells were washed once in serum-free medium and re-suspended thereafter in PBS. Only suspensions consisting of single cells with >90% viability were used for the injections. Mice were injected with 1.5×106 cells sub-cutaneously (S.C) on the right side of hind leg of each mouse using a 23-gauge needle. After tumor transplant, the mice were observed daily for one week, before randomly assigning them to the treatment groups (n=5). The animals thereafter received triptolide (1 mg of triptolide/1 mL of C60-olive oil base) by oral gavage starting on day 15 or on tumor volume reaching ~40-70 mm$^3$. The treatment was continued until ~28 days from first dose. The suggested dose and dosage regimen were based on pilot studies. Tumor size was measured once a week. At the end of the experimental period, the animals were euthanized. As shown in FIG. 11, tumor regression was observed at a dose of 50 µg/kg, 100 µg/kg and 250 µg/kg dose of triptolide.

Example 9: Solubilizing Various Therapeutic Agents

The following therapeutic agents were mixed with the lipofullerene base of Example 3 as follows: about 0.5 gms of paclitaxel in 1000 mL of lipofullerene base; about 0.5 gms of camptothecin in 1000 mL of lipofullerene base; about 0.5 gms of docetaxel in 1000 mL of lipofullerene base; about 0.5 gms of tamoxifen in 1000 mL of lipofullerene base; about 0.5 gms of fulvestrant in 1000 mL of lipofullerene base; about 0.5 gms of vincristine in 1000 mL of lipofullerene base; and about 1 gms of erlotinib in 1000 mL of lipofullerene base.

Each of the above mixtures were sonicated for 30 seconds followed by vortexing for 12 hours in the dark. The solubility of the drug was confirmed by a turbidometer. The Table below shows the fold solubility of the drug in lipofullerene base when compared to its solubility in water.

TABLE 1

| Therapeutic Agent | Water solublity (mg/mL) | Solubility in lipofullerene (mg/mL) | Fold solubility |
|---|---|---|---|
| paclitaxel | 0.00556 | 0.5 | 90 |
| camptothecin | 0.107 | 0.5 | 5 |
| docetaxel | 0 | 0.5 | >100 |
| tamoxifen | 0.00102 | 0.5 | 490 |
| fulvestrant | 0.00672 | 0.5 | 74 |
| vincristine | 0.03 | 0.5 | 17 |
| erlotinib | 0.4 | 1 | 3 |

What is claimed is:

1. A method of making a formulation, the method comprising:
   high-speed blending C60 fullerene with a lipid, wherein the C60 fullerene is present at about 0.1 to about 5 mg per 1 mL of the lipid;
   subsequent to the high-speed blending, stirring the C60 fullerene with the lipid for about 12 hours to about 15 days in absence of light at a temperature of about 25° C. to about 38° C. to form a lipofullerene mixture;
   filtering the lipofullerene mixture;
   adding a poorly soluble anticancer therapeutic agent into the lipofullerene mixture, wherein the therapeutic agent is added in an amount of about 0.01 milligram to about 10 milligrams of the therapeutic agent per 1 mL of the lipofullerene mixture;
   stirring the therapeutic agent into the lipofullerene mixture;
   sonicating the lipofullerene mixture containing the therapeutic agent for about 30 seconds to about 1 hour; and
   subsequent to the sonication, filtering the lipofullerene mixture containing the therapeutic agent.

2. The method of claim 1, wherein the lipid is olive oil.

3. The method of claim 2, wherein the therapeutic agent is triptolide, paclitaxel, camptothecin, docetaxel, tamoxifen, fulvestrant, vincristine, or erlotinib.

4. The method of claim 1, wherein the therapeutic agent is triptolide, paclitaxel, camptothecin, docetaxel, tamoxifen, fulvestrant, vincristine, or erlotinib.

5. The method of claim 1, wherein the lipofullerene mixture has a concentration of greater than 0.8 mg/ml of the C60 fullerene.

6. The method of claim 1, wherein the lipofullerene mixture has a concentration of 2.4 mg/ml of the C60 fullerene.

7. The method of claim 1, wherein the therapeutic agent is triptolide.

8. The method of claim 1, wherein the therapeutic agent is paclitaxel.

9. The method of claim 1, wherein the therapeutic agent is camptothecin.

10. The method of claim 1, wherein the therapeutic agent is docetaxel.

11. The method of claim 1, wherein the therapeutic agent is tamoxifen.

12. The method of claim 1, wherein the therapeutic agent is fulvestrant.

13. The method of claim 1, wherein the therapeutic agent is vincristine.

14. The method of claim 1, wherein the therapeutic agent is erlotinib.

15. The method of claim 1, wherein the stirring of the therapeutic agent into the lipofullerene mixture is performed under inert conditions.

16. The method of claim 1, wherein the formulation is formulated for oral administration.

* * * * *